(12) United States Patent
Zhong et al.

(10) Patent No.: US 8,709,038 B2
(45) Date of Patent: Apr. 29, 2014

(54) PUNCTURE HOLE SEALING DEVICE

(75) Inventors: Sheng-Ping Zhong, Shrewsbury, MA (US); Michael N. Helmus, Worcester, MA (US); Mark T. Ungs, Minnetonka, MN (US); Daniel M. Lafontaine, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1939 days.

(21) Appl. No.: 10/460,747

(22) Filed: Jun. 12, 2003

(65) Prior Publication Data

US 2004/0122350 A1 Jun. 24, 2004

Related U.S. Application Data

(63) Continuation-in-part of application No. 10/325,710, filed on Dec. 20, 2002, now abandoned.

(51) Int. Cl.
*A61B 17/08* (2006.01)

(52) U.S. Cl.
USPC .................................................. 606/213

(58) Field of Classification Search
USPC .............. 606/213, 232, 192, 214; 623/16.11
See application file for complete search history.

(56) References Cited

U.S. PATENT DOCUMENTS

| | | | |
|---|---|---|---|
| 3,438,374 A | 4/1969 | Falb et al. | 128/334 |
| 3,847,652 A * | 11/1974 | Fletcher et al. | 427/491 |
| 4,002,173 A | 1/1977 | Manning et al. | 128/296 |
| 4,068,655 A | 1/1978 | LeRoy | 128/20 |
| 4,140,537 A | 2/1979 | Luck et al. | 106/155 |
| 4,286,341 A * | 9/1981 | Greer et al. | 623/1.4 |
| 4,292,972 A | 10/1981 | Pawelchak et al. | 128/296 |
| 4,365,621 A | 12/1982 | Brundin | 128/1 |
| 4,372,314 A | 2/1983 | Wall | 128/296 |
| 4,390,519 A | 6/1983 | Sawyer | 424/28 |
| 4,404,970 A | 9/1983 | Sawyer | 128/325 |
| 4,405,324 A | 9/1983 | Cruz, Jr. | 604/376 |
| 4,424,208 A | 1/1984 | Wallace et al. | 424/177 |
| 4,509,504 A | 4/1985 | Brundin | 128/1 |
| 4,515,637 A | 5/1985 | Cioca | 424/94 |
| 4,543,410 A | 9/1985 | Cruz, Jr. | 536/84 |
| 4,582,640 A | 4/1986 | Smestad et al. | 260/123 |
| RE32,208 E | 7/1986 | Mattei et al. | 424/78 |
| 4,597,960 A | 7/1986 | Cohen | 424/28 |
| 4,703,108 A | 10/1987 | Silver et al. | 530/356 |

(Continued)

FOREIGN PATENT DOCUMENTS

EP    0 044 624 A1    1/1982
EP    0 145 970 A2    11/1983

(Continued)

OTHER PUBLICATIONS

"Notification of Transmittal of the International Search Report or the Declaration", PCT/US2004/018885.

*Primary Examiner* — Tuan V Nguyen
(74) *Attorney, Agent, or Firm* — Seager, Tufte & Wickhem LLP

(57) ABSTRACT

A hemostatic insert is provided for closing a puncture site in a blood vessel wall. The insert includes an expandable hemostatic member comprising a biocompatible water soluble gel configured to expand from a compressed state when exposed to body fluid and seal the puncture site in the blood vessel wall. A control layer surrounds the hemostatic member and delays expansion of the hemostatic member.

6 Claims, 2 Drawing Sheets

(56) References Cited

U.S. PATENT DOCUMENTS

| | | | |
|---|---|---|---|
| 4,744,364 A | 5/1988 | Kensey | 128/334 |
| 4,749,689 A | 6/1988 | Miyata et al. | 514/21 |
| 4,838,280 A * | 6/1989 | Haaga | 600/564 |
| 4,852,568 A | 8/1989 | Kensey | 128/325 |
| 4,890,612 A | 1/1990 | Kensey | 606/213 |
| 4,979,947 A | 12/1990 | Berman | 604/369 |
| 5,021,059 A | 6/1991 | Kensey et al. | 606/213 |
| 5,061,274 A | 10/1991 | Kensey | 606/213 |
| 5,100,429 A | 3/1992 | Sinofsky et al. | 606/195 |
| 5,108,421 A | 4/1992 | Fowler | 606/213 |
| 5,192,300 A | 3/1993 | Fowler | 606/213 |
| 5,192,302 A | 3/1993 | Kensey et al. | 606/213 |
| 5,254,105 A | 10/1993 | Haaga | 604/265 |
| 5,290,310 A | 3/1994 | Makower et al. | 606/213 |
| 5,292,309 A | 3/1994 | Van Tassel et al. | 604/117 |
| 5,292,332 A | 3/1994 | Lee | 606/213 |
| 5,310,407 A | 5/1994 | Casale | 604/51 |
| 5,320,639 A | 6/1994 | Rudnick | 606/213 |
| 5,324,306 A | 6/1994 | Makower et al. | 606/213 |
| 5,330,445 A * | 7/1994 | Haaga | 604/265 |
| 5,334,216 A | 8/1994 | Vidal et al. | 606/213 |
| 5,376,376 A | 12/1994 | Li | 424/443 |
| 5,383,891 A | 1/1995 | Walker | 606/196 |
| 5,383,897 A | 1/1995 | Wholey | 606/213 |
| RE34,866 E | 2/1995 | Kensey et al. | 606/213 |
| 5,391,183 A | 2/1995 | Janzen et al. | 606/213 |
| 5,431,639 A | 7/1995 | Shaw | 604/264 |
| 5,449,375 A | 9/1995 | Vidal et al. | 606/213 |
| 5,456,693 A * | 10/1995 | Conston et al. | 606/192 |
| 5,460,621 A | 10/1995 | Gertzman et al. | 604/358 |
| 5,486,195 A | 1/1996 | Myers et al. | 606/213 |
| 5,522,840 A | 6/1996 | Krajicek | 606/213 |
| 5,540,715 A | 7/1996 | Katsaros et al. | 606/213 |
| 5,569,297 A | 10/1996 | Makower et al. | 606/201 |
| 5,603,698 A | 2/1997 | Roberts et al. | 604/104 |
| 5,624,669 A | 4/1997 | Leung et al. | 424/78.35 |
| 5,643,318 A | 7/1997 | Tsukernik et al. | 606/214 |
| 5,643,596 A | 7/1997 | Pruss et al. | 424/426 |
| 5,645,849 A | 7/1997 | Pruss et al. | 424/426 |
| 5,702,413 A | 12/1997 | Lafontaine | 606/159 |
| 5,716,375 A * | 2/1998 | Fowler | 606/213 |
| 5,718,916 A * | 2/1998 | Scherr | 424/445 |
| 5,728,132 A | 3/1998 | Van Tassel et al. | 606/213 |
| 5,782,860 A | 7/1998 | Epstein et al. | 606/213 |
| 5,782,861 A | 7/1998 | Cragg et al. | 606/213 |
| 5,823,198 A | 10/1998 | Jones et al. | 128/899 |
| 5,868,762 A | 2/1999 | Cragg et al. | 606/144 |
| 5,895,412 A | 4/1999 | Tucker | 606/215 |
| 5,906,631 A | 5/1999 | Imran | 606/213 |
| 5,964,782 A | 10/1999 | Lafontaine et al. | 606/213 |
| RE36,370 E | 11/1999 | Li | 424/443 |
| 5,980,550 A * | 11/1999 | Eder et al. | 606/191 |
| 5,980,559 A * | 11/1999 | Bonutti | 606/232 |
| 5,984,950 A | 11/1999 | Cragg et al. | 606/216 |
| 6,071,300 A | 6/2000 | Brenneman et al. | 606/213 |
| 6,071,301 A | 6/2000 | Cragg et al. | 606/213 |
| 6,086,607 A | 7/2000 | Cragg et al. | 606/213 |
| 6,162,192 A | 12/2000 | Cragg et al. | 604/15 |
| 6,162,240 A | 12/2000 | Cates et al. | 606/213 |
| 6,183,496 B1 | 2/2001 | Urbanski | 606/213 |
| 6,183,497 B1 | 2/2001 | Sing et al. | 606/213 |
| 6,183,498 B1 | 2/2001 | Devore et al. | 606/214 |
| 6,200,328 B1 | 3/2001 | Cragg et al. | 606/213 |
| 6,238,687 B1 * | 5/2001 | Mao et al. | 424/426 |
| 6,267,761 B1 | 7/2001 | Ryan | 606/50 |
| 6,270,464 B1 | 8/2001 | Fulton, III et al. | 600/562 |
| 6,280,474 B1 * | 8/2001 | Cassidy et al. | 623/16.11 |
| 6,299,619 B1 | 10/2001 | Greene, Jr. et al. | 606/108 |
| 6,315,753 B1 | 11/2001 | Cragg et al. | 604/15 |
| 6,350,274 B1 | 2/2002 | Li | 606/213 |
| 6,440,151 B1 | 8/2002 | Cragg et al. | 606/213 |
| 6,440,153 B2 | 8/2002 | Cragg et al. | 606/213 |
| 6,447,534 B2 | 9/2002 | Cragg et al. | 606/213 |
| 6,500,152 B1 | 12/2002 | Illi | 604/164.07 |
| 6,500,190 B2 | 12/2002 | Greene, Jr. et al. | 606/191 |
| 6,554,851 B1 | 4/2003 | Palasis et al. | 606/213 |
| 6,605,294 B2 * | 8/2003 | Sawhney | 424/426 |
| 6,699,261 B1 * | 3/2004 | Cates et al. | 606/213 |
| 2002/0010150 A1 | 1/2002 | Cortese et al. | 514/54 |
| 2002/0025921 A1 | 2/2002 | Petito et al. | 514/2 |
| 2002/0151918 A1 | 10/2002 | Lafontaine et al. | 606/159 |
| 2003/0004568 A1 * | 1/2003 | Ken et al. | 623/1.46 |
| 2003/0013989 A1 | 1/2003 | Obermiller et al. | 600/567 |
| 2006/0034930 A1 * | 2/2006 | Khosravi et al. | 424/484 |

FOREIGN PATENT DOCUMENTS

| | | |
|---|---|---|
| EP | 0 044 624 B1 | 10/1984 |
| EP | 0467516 A1 | 1/1992 |
| EP | A0645150 * | 3/1995 |
| EP | 0 891 193 B1 | 4/1997 |
| EP | 0 726 749 A2 | 1/2000 |
| EP | 1 269 951 A1 | 1/2003 |
| JP | 55116736 A | 9/1980 |
| JP | 62004232 A | 1/1987 |
| JP | 63070507 A | 4/1988 |
| JP | 02182259 A | 7/1990 |
| JP | 05163157 A | 6/1993 |
| JP | 09294765 A | 11/1997 |
| JP | 2002143210 A | 5/2002 |
| RU | 2122867 C1 | 12/1998 |
| RU | 2135105 C1 | 8/1999 |
| RU | 2165741 C1 | 4/2001 |
| RU | 2178681 C1 | 1/2002 |
| RU | 2179859 C1 | 2/2002 |
| RU | 2180539 C2 | 3/2002 |
| RU | 2185858 C1 | 7/2002 |
| WO | WO 95/12371 | 5/1995 |
| WO | WO 96/40033 | 12/1996 |
| WO | WO 97/37694 | 10/1997 |
| WO | WO 00/29484 | 5/2000 |
| WO | WO 01/82937 A1 | 11/2001 |
| WO | WO 01/97826 A2 | 12/2001 |
| WO | WO 02/09591 A2 | 2/2002 |
| WO | WO 02/09591 A3 | 2/2002 |
| WO | WO 02/054998 A1 | 7/2002 |
| WO | WO 02/072128 A1 | 9/2002 |
| WO | WO 02/096302 | 12/2002 |
| WO | WO 03/002168 A1 | 1/2003 |

* cited by examiner

PUNCTURE HOLE SEALING DEVICE

The present application is a Continuation-In-Part of and claims priority of U.S. patent application Ser. No. 10/325,710, filed Dec. 20, 2002, now abandoned the content of which is hereby incorporated by reference in its entirety.

BACKGROUND OF THE INVENTION

The present invention relates to closing openings in a vessel or other body cavity. More specifically, the present invention relates to an expandable closure device having a barrier coating layer to delay expansion of the device when placed into the body cavity.

There are a wide variety of procedures which require gaining internal access to blood vessels or other body cavities. Many such procedures also require the insertion of treatment devices into the blood vessel or body cavity. Many of these procedures utilize accessible arteries as entry points for the treatment devices. For example, some such arteries include the femoral artery or subclavian artery. There are also a wide variety of procedures which gain access to other body cavities in a minimally invasive fashion.

One problem which must be addressed during these procedures is how to seal or close the opening in the blood vessel or other body cavity once the treatment procedure has been completed. Some prior techniques include simply applying pressure to the opening until it seals itself sufficiently that the pressure may be released. However, this technique often requires that pressure must be consistently applied for an undesirable amount of time after the procedure. Similarly, this type of technique can require a patient's hospitalization to be extended until the treating physician is certain that the closure is complete.

Other techniques have involved suturing the wall of the vessel or body cavity itself. This has typically required the physician to peel back a rather large portion of the tissue surrounding the puncture in order to gain sufficient access to the blood vessel or body cavity that it may be sutured adequately. This can be an undesirably time consuming procedure, and it can result in significant discomfort to the patient.

Still other techniques have involved the insertion of embolic materials adjacent the puncture. Of course, this carries with it its own difficulties. For instances, it is desirable that the embolic material not be placed within a blood vessel or body cavity because this can result in an embolus forming within the blood vessel or body cavity. Similarly, however, it is desirable that the embolic material not be located to far proximal of the puncture because this can result in the blood vessel or body cavity bleeding into the interstitial space proximal of the opening in the blood vessel or body cavity, but distal to the embolic material.

Another technique used to close the opening in the blood vessel or other body cavity once the treatment procedure has been completed is to insert an expandable hemostatic member into the opening. For example, the member can be at least sponge-like material which expands to fill the opening thereby close the opening. However, it can be difficult to properly place the expandable member in the opening because in its expanded state, the member has a size which is greater than that provided by the opening.

SUMMARY OF THE INVENTION

An apparatus for closing a puncture site in a blood vessel wall includes an expandable hemostatic member comprising a biocompatible hydrophilic or water absorbing matrix configured to expand from a compressed or contracted state when exposed to body fluid and thereby seal the puncture site in the blood vessel wall. A control layer surrounds the hemostatic member and delays expansion of the hemostatic member from the compressed/contracted state after exposure to body fluid. The control layer can be of appropriate water soluble materials.

DETAILED DESCRIPTION OF THE PREFERRED EMBODIMENTS

Figure 1:
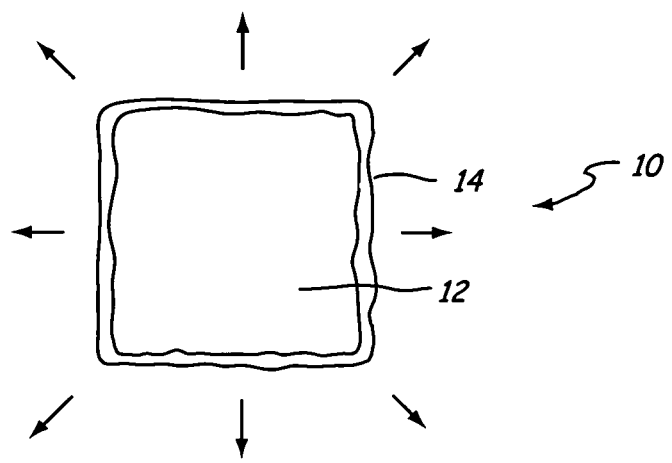
FIG. 1 is a side cross-sectional view of a hemostatic insert in accordance with the present invention.

FIG. 1 is a cross-sectional view of a hemostatic insert 10 comprising an expandable hemostatic member 12 surrounded by a control layer 14.

The expandable hemostatic member 12 is shown in a contracted state and is configured to expand upon exposure to body fluid. The present invention provides an improved hemostatic insert 10 for closing a puncture site such as those created through interventional angioplasty. The control layer 14 delays the expansion of the expandable hemostatic member 12 when exposed to body fluid This allows the hemostatic insert 10 to be placed into the puncture site and positioned as desired in a compressed state. This overcomes drawbacks associated with prior art hemostatic collagen/gelatin sponges in which the sponge swells before reaching the puncture site. When in the contracted state, the member 12 has a volume that is less than when in the expanded state. The change in volume can be through any appropriate technique. The present invention makes delivery of the hemostatic insert 10 easier and reduces the likelihood that the member is damaged or otherwise compromised during the insertion process. Because the member 12 has a smaller volume in the contracted state and can be easily introduced through a small opening. Further, the control layer 14 can provide a smooth and/or lubricious surface which promotes insertion into the puncture site.

Figure 2:
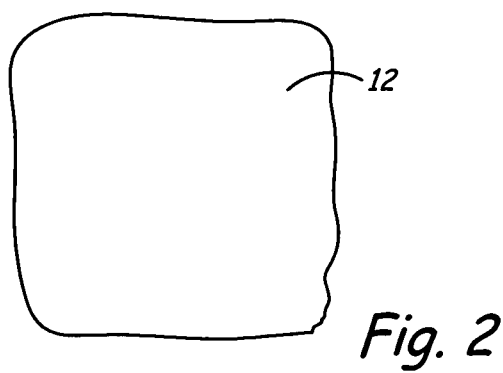
FIG. 2 is a side view of an expandable hemostatic member after the member has expanded.

FIG. 2 is a side view of the expandable hemostatic member 12 following expansion due to exposure to liquid. The expansion occurs in the direction indicated by the arrows show in FIG. 1. In one embodiment, the control layer 14 comprises a removable or protective coating which dissolves or otherwise loosens from the surface of the expandable hemostatic member 12. For example, the control layer 14 can dissolve when exposed to body fluid such as blood. In another example, the control layer 14 provides a barrier to liquid which slows the entry of liquid to the expandable hemostatic member 12. In general, the controlled layer 14 delays the penetration of liquid to the expandable hemostatic member 12. The layer 14 eventually dissolves or otherwise allows liquid to enter the member 12 which responsively swells to its full size as illustrated in FIG. 2. This allows the sealing of the puncture site to be achieved in a more controlled fashion.

In general, the expandable hemostatic member 12 is of a biocompatible material which expands when exposed to liquid. Similarly, the control layer should be of a biocompatible material which delays penetration of the liquid into the member 12. The control layer of 12 may be softening or soluble upon contact of body fluid. The layer 12 may further become lubricious when exposed to body fluid. In one example, member 12 comprises a collagen/gelatin sponge. The member 12 can be a gel formed from denatured collagen, foam, solid or a sponge matrix. Natural or synthetic polymer gels may also be employed. During the expansion, the member 12 provides a outwardly directed force such that it seals against the walls of the opening and is secured therein. During typical surgical applications, the member 12 should expand sufficiently in less than a few minutes after exposure to water. However, in some embodiments, it may be desirable for the delay to be significantly longer, for example, days or even weeks.

In one example, the member 12 comprises a sponge material which is coated with alginate and then cross linked with a low concentration of calcium. This provides a multi-valient cation cross linked alginate which is not water soluble and which has relatively low water permeability. However, the cross linking of the alginate by a multi-valient such as calcium is reversible when it is exposed to sequestrants. When the cross linked alginate is introduced into a patient, the calcium is removed by body fluid, and the alginate dissolves. After the alginate protective layer has been partially or completely removed, the body fluid enters the expandable hemostatic member 12. This causes member 12 to swell and thereby seal the puncture hole. Further, the characteristics of the dissolving of the algen, and the expansion of the expandable hemostatic member 12, can be controlled by controlling the alginate composition, the cross linking density, the coating thickness of the control layer 14 and other parameters.

In one specific example, a 1% alginate (molecular weight 2 million) aqueous solution is applied to a collagen sponge by spraying. The solution is allowed to dry. In another example, between 0.2% and a 3% alginate aqueous solution is used. Next, 20% calcium chloride aqueous solution is sprayed onto the dried alginate. In another example, between a 5% and a 30% calcium chloride aqueous solution is used. The calcium chloride solution is then allowed to dry. The thickness of the alginate/calcium protective layer is preferably between about 1 and about 5 microns. The resultant control layer operates in accordance with the present invention and allows controlled swelling of the collagen sponge.

In another specific example, a collagen sponge is coated, with a cellulous composition such as high molecular weight hydroxyl propyl cellulose (HPC). The HPC forms a thin shell on the exterior of the sponge. When the HPC is exposed to liquid, the HPC is slowly hydrated and dissolves. HPC swells as the liquid moves through the coating until the liquid reaches the expandable member 12. This causes expandable member 12 to expand. The expansion causes further disruption of the HPC coating allowing more rapid expansion of member 12. Any appropriate coating system can be used. Other polymer systems that act in this manner include hydroxypropylmethyl cellulose, high molecular weight polyethylene oxide, copolymers of methylvinyl ether, maleic anhydride and other plastic water soluble type materials. A cross-linked hydrogel system allows water to permeate the coating and swelling of the expandable hemostatic member 12 will occur if the coating is friable. In some embodiments, a rapidly hydrolizing polymer can be used. In some embodiments, a longer delay may be desirable, for example, to allow healing of adjacent tissue prior to full expansion of the member 12. The time delay due to the HPC layer can be controlled by the molecular weight of the HPC, the thickness of the HPC and by including additives in the HPC, for example. In one specific embodiment, a 5% (preferably between 1% and 8%) HPC aqueous solution (molecular weight 1.5 million) is spray coated onto a collagen sponge and allowed to dry.

Although spray coatings have been described, other coating techniques can be used including dipped coatings, suspension coatings, fluidized coatings, plasma coatings, etc. Further other types of ultra hyrophilic polymers can be used as a control layer 14 such as high molecular weight polyacrylic acid, acrylic acid/acrylamide copolymer, polyhydroxylethyl methacrylate (polyHEMA) (molecular weight greater than 1 million, etc. In embodiments in which the control layer 12 dissolves, the dissolved material should also be biocompatible.

Figure 3:
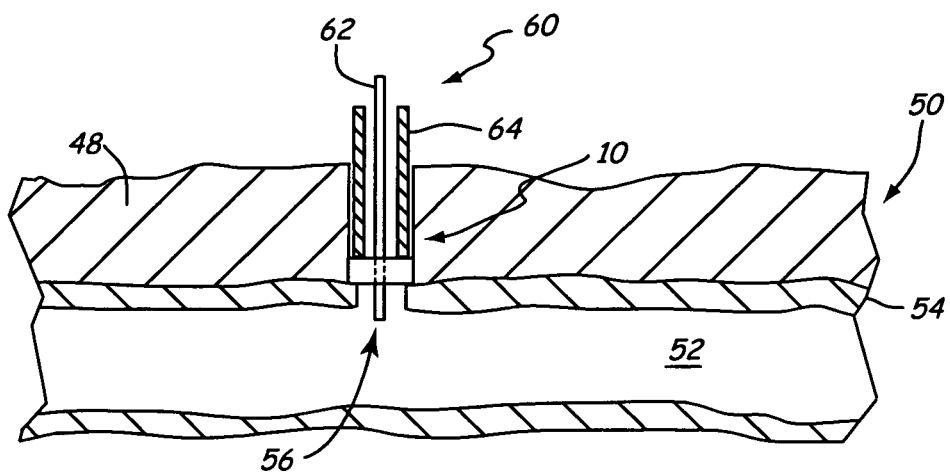
FIG. 3 is a cross-sectional view of a blood vessel showing insertion of the hemostatic insert of FIG. 1.

As discussed above, the hemostatic insert 10 is used to seal puncture sites in a patient. FIG. 3 is a side cross-sectional view of a portion of a blood vessel 50 and tissue 48. While the present invention can be used with substantially any body cavity, a blood vessel is described herein for exemplary purposes only. Blood vessel 50 has a lumen 52 defined by blood vessel wall 54. Blood vessel wall 54 and tissue 48 are shown as having an opening 56 formed therein. Opening 56 can be an opening which was made, for example, in order to perform a treatment procedure during which access to lumen 52 is needed.

FIG. 3 also illustrates a closure apparatus 60 which includes an elongate member 62 which extends through a hole in hemostatic insert 10. Hemostatic insert 10 is frictionally engaged with the distal tip of elongate member 62. However, other techniques and mechanisms can be used to secure the hemostatic insert 10. A slidable pusher 64 slides along elongate member 62. To seal the opening 56, the hemostatic member 10 is placed in opening 56 adjacent wall 54 of the blood vessel 50 using elongate member 62. Once the hemostatic member 10 is properly positioned, the pusher 64 is used to maintain the position of hemostatic insert 10 at the puncture site while elongate member 62 is withdrawn from insert 10. This withdrawal process can occur prior to the expansion of the expandable member 12, during expandable member 12, or after expandable member 12 has fully expanded.

Figure 4:
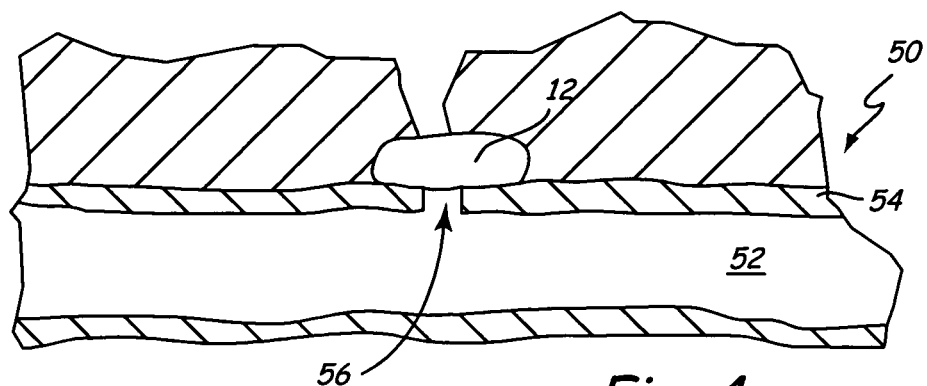
FIG. 4 is a side cross-sectional view of the blood vessel of FIG. 3 following expansion of an expandable hemostatic member to seal an opening in the blood vessel.

FIG. 4 is a cross-sectional view of blood vessel 10 showing expandable hemostatic member 12 expanded from the contracted state shown in FIG. 3. Hemostatic member 12 is shown sealing the opening 56 in blood vessel wall 54.

The particular insertion method and apparatus shown in FIGS. 3 and 4 is for illustration purposes only and any appropriate technique and apparatus may be used with the present invention.

Although the present invention has been described with reference to preferred embodiments, workers skilled in the art will recognize that changes may be made in form and detail without departing from the spirit and scope of the invention. Although the protective layer 14 is described as being responsive to exposure to liquid, other techniques can also be used to trigger expansion of expandable hemostatic member 12. These techniques include exposure to heat, radio signals, radiation, ultrasonic signals, chemicals, etc. In another aspect, the control layer provides a desired shape to the hemostatic insert. For example, the control layer can be used to provide a pointed shape which allows for easier insertion of the hemostatic layer into the puncture site. The control layer can be from water soluble materials used in the pharmaceutical industry that includes materials such as maleic anhydrides and water soluble acrylics. Water soluble coatings (acrylic, cellulosic) can be obtained from Eastman, BASF, Rhom, Poulenc, and other sources.

What is claimed is:

1. An apparatus for closing a puncture site adjacent to a blood vessel wall comprising:
   an expandable hemostatic member formed of a biocompatible member, said hemostatic member having a first contracted state and a second expanded state and being configured to expand from the first contracted state to the second expanded state when exposed to body fluid; and
   a control layer substantially covering the entire surface of the hemostatic member, the control layer having an initial state, in which the control layer prevents body fluid from reaching the hemostatic member, and an activated state in which the control layer no longer prevents body fluid from reaching the hemostatic member, said control layer being configured to change from the initial state to the activated state in response to an expansion triggering technique including exposure to radio signals, radiation, or ultrasonic signals;
   wherein the change from the initial state to the activated state delays penetration of body fluid through the control layer to the expandable hemostatic member, further wherein the hemostatic member in the first contracted state and the control layer in the initial state are sized and configured to be disposed in an opening in body tissue in a desired position adjacent a wall of a blood vessel.

2. The apparatus of claim 1, wherein the expandable hemostatic member comprises collagen.

3. The apparatus of claim 1, wherein the control layer has a thickness of between about 1 and 200 microns.

4. The apparatus of claim 1, further comprising an elongate member which extends through a hole in the expandable hemostatic member.

5. The apparatus of claim 4, wherein the elongate member frictionally engages the expandable hemostatic member.

6. The apparatus of claim 4, further comprising a slidable pusher member capable of maintaining the expandable hemostatic member in the desired position while the elongate member is withdrawn through the hole in the expandable hemostatic member.

* * * * *